United States Patent
Dai et al.

(10) Patent No.: US 7,416,699 B2
(45) Date of Patent: *Aug. 26, 2008

(54) CARBON NANOTUBE DEVICES

(75) Inventors: Hongjie Dai, Sunnyvale, CA (US); Jing Kong, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 927 days.

This patent is subject to a terminal disclaimer.

(21) Appl. No.: 10/175,026

(22) Filed: Jun. 18, 2002

(65) Prior Publication Data

US 2002/0179434 A1   Dec. 5, 2002

Related U.S. Application Data

(60) Division of application No. 09/574,393, filed on May 19, 2000, now Pat. No. 6,528,020, which is a continuation-in-part of application No. 09/133,948, filed on Aug. 14, 1998, now Pat. No. 6,346,189.

(60) Provisional application No. 60/171,200, filed on Dec. 15, 1999.

(51) Int. Cl.
*B32B 5/02* (2006.01)
*B32B 27/04* (2006.01)
*B32B 27/12* (2006.01)
*G01N 27/06* (2006.01)
*G01N 27/12* (2006.01)

(52) U.S. Cl. .................. 422/82.02; 977/700; 977/742; 977/745; 977/750; 977/752; 977/746; 422/50; 422/56; 422/57; 422/58; 422/68.1; 422/69; 422/82.01; 422/83; 422/98; 436/43; 436/63; 436/64; 436/68; 436/145; 436/149; 436/72; 436/73; 436/150; 436/151; 73/1.01; 73/53.01; 438/48; 438/49

(58) Field of Classification Search .................. 422/50, 422/56, 57, 58, 68.1, 69, 82.01, 82.02, 83, 422/88, 90, 98; 436/43, 63, 64, 68, 145, 436/149, 72, 73, 150, 151; 73/1.01, 1.02, 73/23.2, 53.01; 438/48, 49; 977/700, 742, 977/745, 746, 750, 752
See application file for complete search history.

(56) References Cited

U.S. PATENT DOCUMENTS

| | | |
|---|---|---|
| 4,495,793 A | 1/1985 | Hager |
| 5,282,950 A | 2/1994 | Dietze et al. |
| 5,334,351 A | 8/1994 | Heinze |
| 5,395,504 A | 3/1995 | Saurer et al. |
| 5,407,554 A | 4/1995 | Saurer |
| 5,436,167 A | 7/1995 | Robillard |
| 5,448,906 A | 9/1995 | Cheung |
| 5,525,297 A | 6/1996 | Dinger et al. |
| 5,571,395 A | 11/1996 | Park et al. |
| 5,626,650 A | 5/1997 | Rodriguez et al. |
| 5,653,951 A | 8/1997 | Rodriguez et al. |
| 5,660,791 A | 8/1997 | Brenneman |
| 5,726,524 A | 3/1998 | Debe |
| 5,797,693 A | 8/1998 | Jaeger |
| 5,810,199 A | 9/1998 | Charlton et al. |
| 5,830,326 A | 11/1998 | Iijima et al. |
| 5,866,434 A | 2/1999 | Massey et al. |
| 5,872,422 A | 2/1999 | Xu |
| 5,872,713 A | 2/1999 | Douglas et al. |
| 5,891,395 A | 4/1999 | Glaunsinger et al. |
| 5,962,863 A * | 10/1999 | Russell et al. .................. 257/14 |
| 6,012,327 A | 1/2000 | Seth et al. |

| | | | |
|---|---|---|---|
| 6,105,417 A | 8/2000 | Nosaka et al. | |
| 6,162,926 A | 12/2000 | Murphy et al. | |
| 6,190,634 B1 * | 2/2001 | Lieber et al. | 423/439 |
| 6,346,189 B1 * | 2/2002 | Dai et al. | 205/766 |
| 6,445,006 B1 * | 9/2002 | Brandes et al. | 257/76 |
| 6,528,020 B1 * | 3/2003 | Dai et al. | 422/98 |
| 6,628,053 B1 * | 9/2003 | Den et al. | 313/310 |
| 6,630,772 B1 * | 10/2003 | Bower et al. | 313/311 |
| 6,720,728 B2 * | 4/2004 | Den et al. | 313/495 |

FOREIGN PATENT DOCUMENTS

| | | |
|---|---|---|
| DE | 2652370 | 5/1978 |
| DE | 29620368 U1 | 3/1997 |
| DE | 19639226 A1 | 3/1998 |
| DE | 19715031 A1 | 10/1998 |
| EP | 0373413 | 6/1990 |
| EP | 0455508 A1 | 11/1991 |
| EP | 0732590 A2 | 9/1996 |
| EP | 0738666 A2 | 10/1996 |
| EP | 0811843 A2 | 12/1997 |
| EP | 0877250 A2 | 11/1998 |
| EP | 0909952 A2 | 4/1999 |
| JP | 06310976 A | 11/1994 |
| WO | WO92/17778 | 10/1992 |
| WO | WO94/10558 | 5/1994 |
| WO | WO94/19685 | 9/1994 |
| WO | WO97/48979 | 12/1997 |
| WO | WO98/19159 | 5/1998 |
| WO | WO99/13100 | 3/1999 |

OTHER PUBLICATIONS

Chen, R.J. "Molecular photodesorption from single-walled carbon nanotubes" Applied Physics Letters, Oct. 2001, vol. 79, No. 14, pp. 2258-2260.

Koshio, A. et al, "In situ laser-furnace TOF mass spectrometry of C36 and the large-scale production by arc-discharge" J. Phys. Chem. B, Jul. 2000, vol. 104, pp. 7908-7913, especially pp. 7908-7909.

Soh, Hyongsok T. et al. *Applied Physics Letters*. vol. 75, No. 5, 627-629 (Aug. 1999).

Tans, Sander J. et al. *Nature*. vol. 393, 1-3 (May 1998).

Lee, R.S. et al. *Nature*. vol. 338, 255-257 (Jul. 1997).

Kong, Jing et al. *Nature*. vol. 395, No. 6705. 878-881 (Oct. 1998).

* cited by examiner

*Primary Examiner*—Brian J Sines
(74) *Attorney, Agent, or Firm*—Crawford Maunu PLLC

(57) ABSTRACT

Nanotubes and nanotube-based devices are implemented in a variety of applications. According to an example embodiment of the present invention, a nanotube is adapted to pass current between two conductive elements. In one implementation, each conductive element includes a catalyst material, wherein electrical connection is made to opposite ends of the nanotube at each of the catalyst portions. In one implementation, the electrical connection is used to detect an electrical characteristic of the nanotube, such as the response of the nanotube to exposure to one or more of a variety of materials. In another implementation, the nanotube is used for chemical and biological sensing. In still another implementation, a particular functionality is imparted to the nanotube using one or more of a variety of materials coupled to the nanotube, such as metal particles, biological particles and/or layers of the same.

28 Claims, 9 Drawing Sheets

CARBON NANOTUBE DEVICES

RELATED PATENT DOCUMENTS

This is a divisional of U.S. patent application Ser. No. 09/574,393, filed on May 19, 2000, now U.S. Pat. No. 6,528,020 issued on Mar. 4, 2003 and entitled "Carbon Nanotube Devices," which claims benefit of U.S. Provisional Patent Application Ser. No. 60/171,200 filed on Dec. 15, 1999. U.S. patent application Ser. No. 09/574,393 is further a continuation-in-part of U.S. patent application Ser. No. 09/133,948, filed on Aug. 14, 1998, now U.S. Pat. No. 6,346,189 issued on Feb. 12, 2002 and entitled "Carbon Nanotube Structures Made Using Catalyst Islands," all of which are fully incorporated herein by reference.

FEDERALLY SPONSORED RESEARCH OR DEVELOPMENT

This invention was made with Government support under 9871947 awarded by the National Science Foundation. The Government has certain rights in this invention.

FIELD OF THE INVENTION

The present invention relates generally to carbon nanotube devices and more particularly to chemical and biological sensors and related applications employing carbon nanotubes.

BACKGROUND

Carbon nanotubes are unique carbon-based, molecular structures that exhibit interesting and useful electrical properties. There are two general types of carbon nanotubes, referred to as multi-walled carbon nanotubes (MWNTs) and single-walled carbon nanotubes (SWNTs). SWNTs have a cylindrical sheet-like, one-atom-thick shell of hexagonally-arranged carbon atoms, and MWNTs are typically composed of multiple coaxial cylinders of ever-increasing diameter about a common axis. Thus, SWNTs can be considered to be the structure underlying MWNTs and also carbon nanotube ropes, which are uniquely-arranged arrays of SWNTs.

Due to their unique electrical properties, carbon nanotubes are being studied for development in a variety of applications. These applications include, among others, chemical and bio-type sensing, field-emission sources, selective-molecule grabbing, nano-electronic devices, and a variety of composite materials with enhanced mechanical and electromechanical properties. More specifically, for example, in connection with chemical and biological detection, carbon nanotubes are being studied for applications including medical devices, environmental monitoring, medical/clinical diagnosis and biotechnology for gene mapping and drug discovery. For general information regarding carbon nanotubes, and for specific information regarding SWNTs and its applications, reference may be made generally to the above-mentioned patent documents, and also to: "Carbon Nanotubes: Synthesis, Structure, Properties and Applications," M. S. Dresselhaus, G. Dresselhaus and Ph. Avouris (Eds.), Springer-Verlag Berlin Heidelberg, New York, 2001;and "T. Single-shell Carbon Nanotubes of 1-nm Diameter," Iijima, S. & Ichihashi, Nature 363, 603-605 (1993).

Sensing chemical and biological species plays an important role in many industrial, agricultural, medical, and environmental processes. Detection of $NO_2$ gas, for example, provides a crucial measure of environmental pollution due to combustion or automotive emissions. In industrial, medical and living environments, the amount of $NH_3$ also needs to be closely monitored. Moreover, there is a growing need to detect biological species in a variety of biomedical applications. However, previously-used sensors typically must operate at elevated temperatures to enhance chemical reactivity, and often require long recovery times (if recoverable at all), poor reproducibility, and are applicable to the detection of a very limited range of chemical species.

Many electronic devices benefit from small-scale electronic circuits and arrangements, and also play in important role in a variety of applications. The size and electrical properties of nanotubes including carbon nanotubes make them potentially useful for such small-scale devices. However, previously-available nanotubes have been difficult to manufacture and implement in a variety of such applications.

SUMMARY

The present invention is directed to overcoming the above-mentioned challenges and others related to carbon nanotube devices and their implementations. The present invention is exemplified in a number of implementations and applications, some of which are summarized below.

According to an example embodiment of the present invention, a nanotube device includes a nanotube extending between two conductive elements. The conductive elements are coupled to one or more of a variety of circuit elements, such as those typically found in sensors and integrated circuit devices. The nanotube device is responsive to a variety of electrical, physical and chemical stimuli, and is adaptable for implementation with many applications, such as for sensing and nanoelectronic applications.

In one example embodiment of the present invention, the nanotube device discussed above is used in chemical and biological sensor applications. In another example embodiment of the present invention, individually separable nanotubes are grown in a controlled fashion. In another example embodiment of the present invention, the nanotube device is manipulated and integrated into a functional device such as an electrical, mechanical and/or electrochemical device that can be individually tailored to a wide range of applications. In still another example embodiment of the present invention, the nanotube device is modified to tune its sensitivity to a variety of molecular and/or biological species using one or more materials disposed on the nanotube. With these and other approaches, electrical, mechanical, and electrochemical nanotube devices, including those employing carbon nanotubes, can be individually tailored to a wide range of applications. In addition, these nanotube devices demonstrate significant and robust response, and more significantly, tunable selectivity to chemical or biological species in selected environments.

According to another example embodiment of the present invention, a nanotube device includes a substrate with two catalyst islands disposed thereon. Each catalyst island is adapted for growing nanotubes when exposed to a hydrocarbon gas at elevated temperatures. Using this approach, at least one nanotube is formed between, with its two ends rooted in, the two catalyst islands. Metal electrodes are then placed to fully cover the catalyst islands and the two ends of the bridging nanotube. The metal electrodes are useful, for example, for electrically coupling the nanotube to other circuitry, such as for measuring an electrical response of the nanotube. In one particular implementation, the nanotube device is coated and/or decorated with one or more sensing agents, such as metal particles, polymers, and biological species, which imparts sensitivity to the nanotube for particular molecular species.

In another example embodiment of the present invention, the selectivity of the nanotube to chemical species is physically tuned for exhibiting a selected response, for example, by applying a gating voltage to a nanotube. The gating voltage effectively shifts the Fermi energy level of the nanotube, giving rise to change in electrical conductivity of the nanotube upon adsorption of foreign chemical species. With this approach, a gating voltage can be applied to the nanotube, for example, to achieve a particular response of the nanotube to the presence of selected chemical species.

In another example embodiment of the present invention, a nanotube device comprises a substrate covered with a layer of catalyst material. The catalyst enables the growth of nanotubes when exposed to a hydrocarbon gas at elevated temperatures, yielding a film of interconnected nanotubes disposed on the substrate. Two metal electrodes (e.g., an alloy of nickel-gold, or titanium-gold) are then deposited onto the two opposing sides of the film, separated by a gap devoid of any metal. Such a nanotube film device can be easily produced in a scaled-up fashion with low cost. For instance, in one implementation, the substrate is made of quartz and the catalyst comprises $Fe_2O_3$ and alumina nanoparticles. Nanotubes thus produced are generally single-walled carbon nanotubes that are semiconducting and/or metallic.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1A:
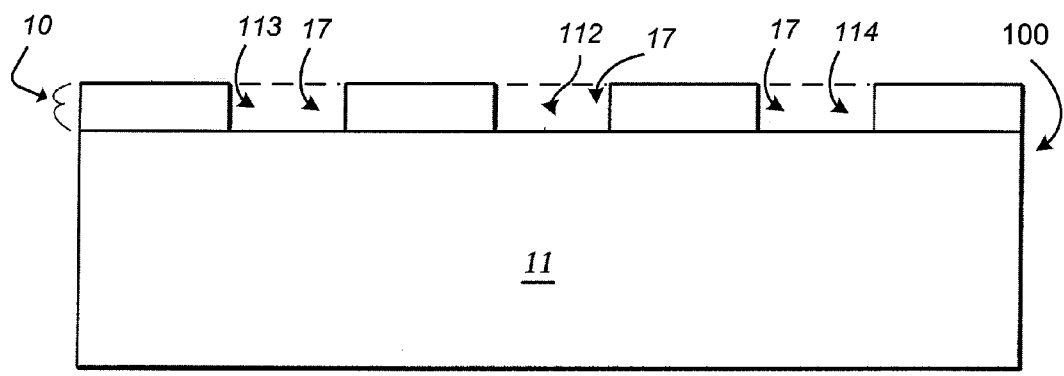
FIGS. 1A-1C depict a method for synthesizing individually distinct nanotubes on a substrate, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of different types of devices, and the invention has been found to be particularly suited for carbon nanotube-based sensors and sensing applications, such as for sensing chemical and biological species. While the present invention is not necessarily limited to such applications, various aspects of the invention may be appreciated through a discussion of various examples using this context.

In connection with an example embodiment of the present invention, it has been discovered that a nanotube device including a nanotube having electrodes at opposite ends thereof exhibits characteristics useful in a variety of implementations. In various implementations, the nanotube is altered physically, chemically or electrically, such as by coating with a metal or other substance or by applying a gating voltage thereto. These alterations tailor the nanotube device to particular applications, such as for making the nanotube respond electrically to a particular molecular species or for making the nanotube respond electrically in a manner similar to semiconducting substrates. With these approaches, the nanotube device can be implemented in a variety of applications. For more information regarding nanotubes, and methods of fabrication thereof, that can be used in connection with the present invention, reference may be made to "Synthesis of Single Single-Walled Carbon Nanotubes on Patterned Silicon Wafers," J. Kong, H. T. Soh, A. Cassell, C. F. Quate, and H. Dai, *Nature*, 395, 878 (1998)., which is fully incorporated herein by reference.

In one example embodiment of the present invention, a carbon nanotube extends between two electrodes and over a semiconductor substrate, such as doped silicon with a layer of oxide formed thereon. The electrodes include a catalyst material, such as, $Fe_2O_3$ and alumina nanoparticles, and a conductive material disposed thereon, thereby forming conductive catalyst islands (e.g., about 3-5 microns in cross-sectional length). In one implementation, the nanotube is a single-walled carbon nanotube. In another implementation, the metal electrodes include an alloy such as nickel-gold or titanium-gold.

Figure 1B:
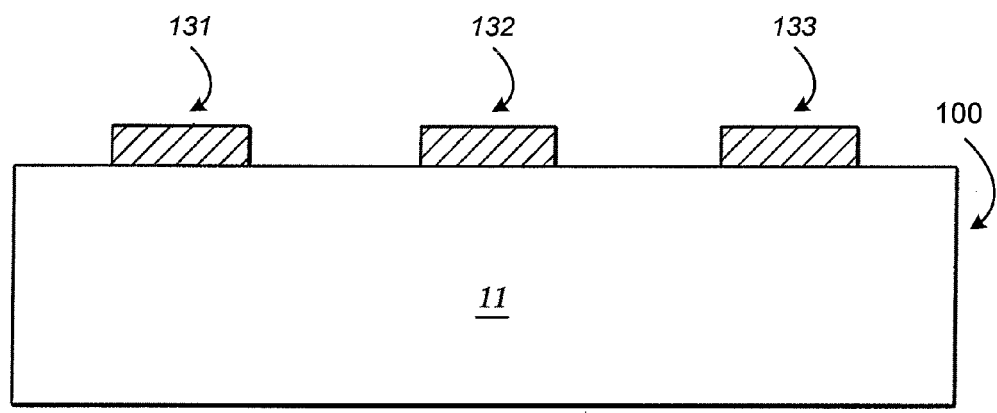
Figure 1C:
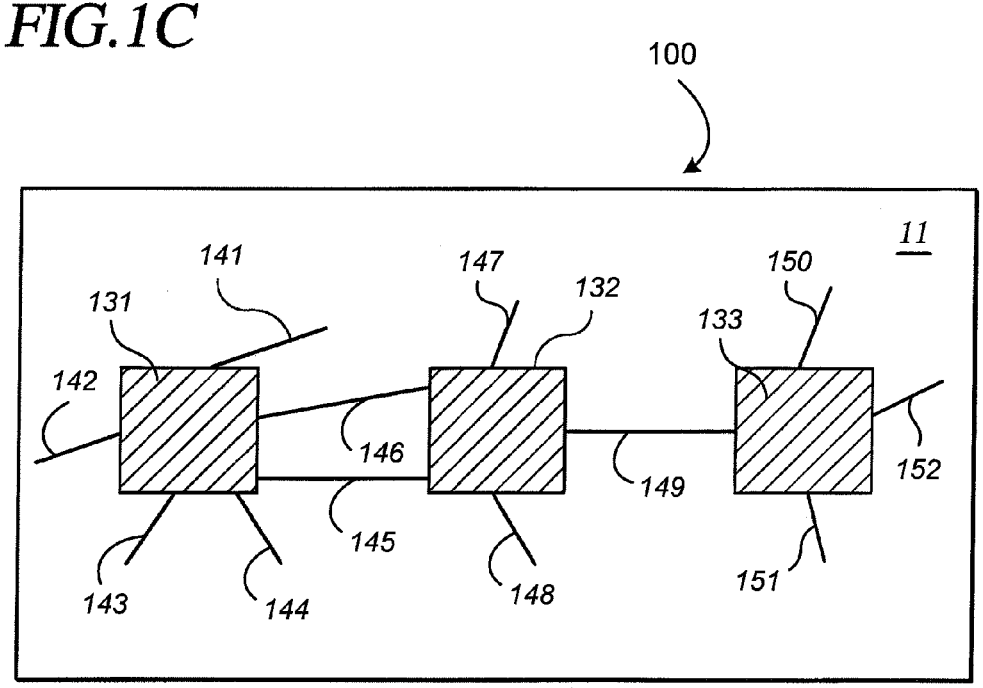

FIGS. 1A-1C show a carbon nanotube device 100 at various stages of manufacture, with individually distinct nanotubes being formed over a silicon substrate 11, according to another example embodiment of the present invention. In FIG. 1A, a layer of resist 10 is disposed and patterned on a top surface of the substrate 11. The substrate 11 may include, for example, one or more of silicon, alumina, quartz, silica, silicon nitride and/or doped silicon with a layer of native oxide formed thereon. The resist 10 is patterned using one or more commonly-available techniques, such as electron-beam lithography, to form a patterned resist structure with openings 112, 113 and 114 therein that expose the underlying substrate 11. The size of the openings is selected for controlling the size of catalyst islands to be subsequently filled therein, and in one implementation, the openings are about 5 microns in diameter and spaced at a distance of about 10 microns. Catalyst material 17 is formed in the openings 112, 113 and 114 and over the substrate 11, filling the openings as shown by dashed lines. In one implementation, the catalyst material 17 includes about 15 mg of alumina nanoparticles, about 0.05 mmol of $Fe(NO_3)39H_2O$, and about 0.015 mmol of $MoO_2(acac)_2$ mixed in about 15 ml of methanol.

In FIG. 1B, the remaining portion of the resist layer 10 is lifted off after the catalyst material 17 is formed in the openings 112, 113 and 114, and in the instance where solvent (i.e., methanol) is used in forming the catalyst material, after the solvent dries. An array of isolated catalyst islands including islands 131, 132 and 133 thus remains over the substrate 11, with the number, size and orientation of catalyst islands being selected via the formation of the patterned layer of resist 10.

After the catalyst islands are formed, the nanotube device 100 is heated to above about 900 degrees Celsius (e.g., in a tube furnace) while exposed to a flow of methane to decompose the $Fe(NO_3)_3$ to a $Fe_2O_3$/nanoparticle (e.g., alumina nanoparticles) mixture, with results shown in FIG. 1C. The $Fe_2O_3$/nanoparticle mixture catalyzes the growth of carbon nanotubes when exposed to the methane gas at the elevated temperature and a plurality of carbon nanotubes 141-152 are grown as shown. The catalyst islands 131, 132 and 133 optionally include a material such as iron, molybdenum, cobalt, nickel, ruthenium, zinc and oxides thereof, and in one implementation, the catalyst islands are coated with a metal for tailoring the device 100 for use in sensing chemicals. With these approaches, the carbon nanotubes grown are predominantly individually distinct, single-walled nanotubes with few structural defects and are substantially straight, typically extending up to more than 10 microns in length with diameters ranging from 1-3 nanometers. Moreover, a number of the carbon nanotubes formed bridge adjacent islands, such as the carbon nanotubes 145, 146 and 149. Such a nanotube bridge forms when a tube growing from one catalyst island falls on and interacts with another island during the synthesis process as described above. These bridged nanotubes are useful for a variety of implementations, including those discussed below.

Nanotube-based chips produced using the techniques discussed in connection with FIGS. 1A-1C can be incorporated into a variety of electronic and mechanical devices. In one particular implementation, nanotubes bridging two catalyst islands are cut mechanically or electrically using an AFM (atomic force microscopy) tip to form a device having a single nanotube bridging two catalyst islands. Electron-beam lithography is then employed to deposit metal electrodes onto the two catalyst islands bridged by the nanotube, with the metal electrodes including, for example, an alloy of nickel-gold or titanium-gold. In one implementation, the metal electrodes are formed of about 20 nanometers of nickel with 60 nanometers gold on top of the nickel. These electrodes provide electrical connections between the nanotube and macroscopic electronic circuits.

Figure 2:
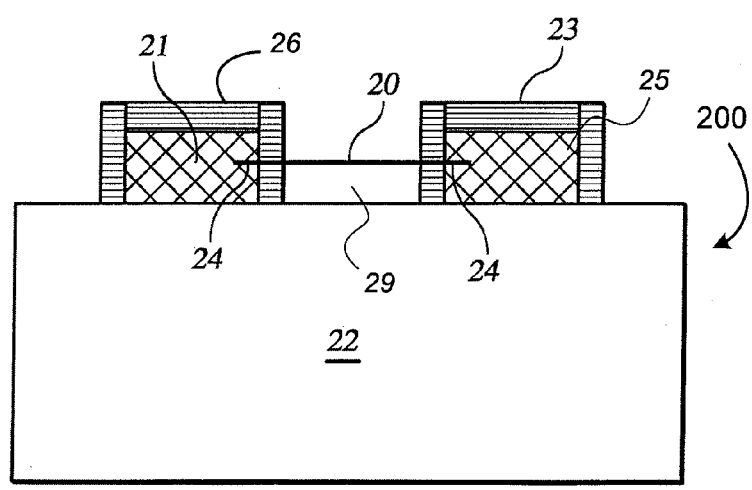
FIG. 2 is a nanotube device comprising a single nanotube, according to another example embodiment of the present invention.

FIG. 2 shows a nanotube device single nanotube 20 disposed between two catalyst islands 21 and 25 on a substrate 22, according to another example embodiment of the present invention. The catalyst islands 21 and 25 and the carbon nanotube 20 may be formed, for example, in a manner similar to that described above in connection with FIGS. 1A-1C. In addition, in one implementation, the nanotube 20 is formed on the substrate 22. Two metal electrodes 23 and 26 are formed over the catalyst islands 21 and 25 and contacting opposite ends of the carbon nanotube 20. Electrical contact can then made across the carbon nanotube 20 via the electrodes 23 and 26 for detecting electrical characteristics of the carbon nanotube 20, such as for detecting a response of the carbon nanotube to exposure to a particular molecular species. A gate 29 is optionally disposed below the nanotube 20 and configured and arranged to apply a voltage signal to the nanotube 20 for controlling electrical characteristics thereof.

Figure 3A:
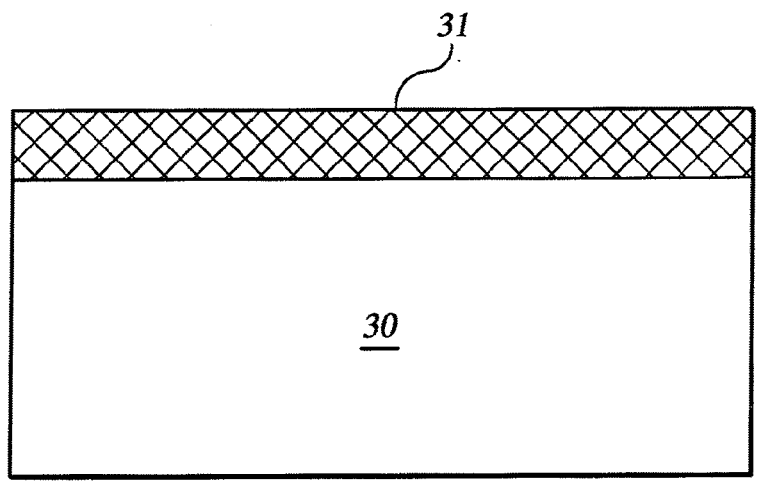
FIGS. 3A-3B show a method for making a nanotube film device, according another example embodiment of the present invention.
Figure 3B:
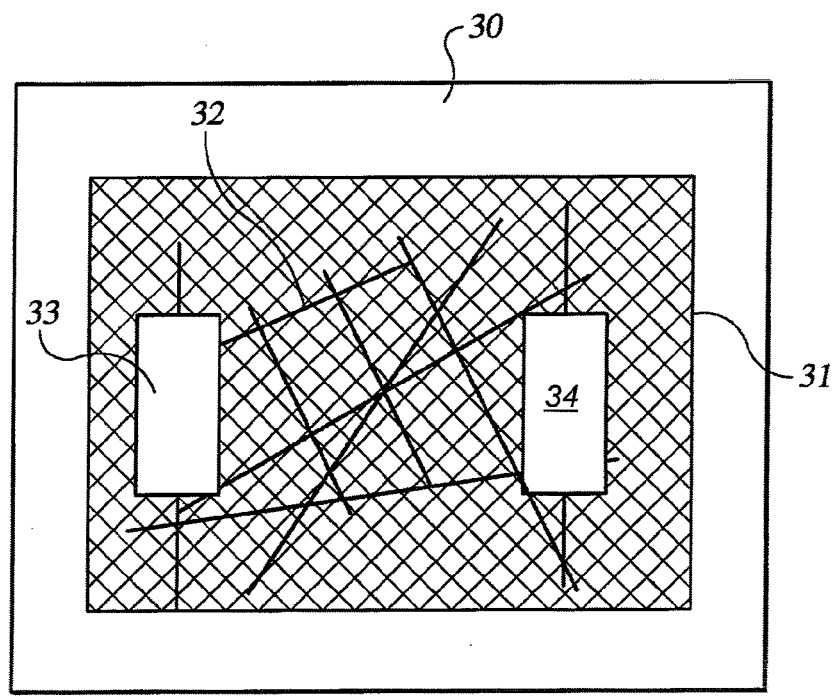

FIGS. 3A-3B show front and top views, respectively, of a film of nanotubes at stages of synthesis on a substrate, according to another example embodiment of the present invention. In FIG. 3A, a layer of catalyst 31 is spin-coated over a substrate 30, such as a substrate including one or more of: silicon, alumina, quartz, silica and silicon nitride. In one implementation, the catalyst 31 is prepared by mixing 15 mg of alumina nanoparticles, 0.05 mmol of $Fe(NO_3)39H_2O$, and 0.015 mmol of $MoO_2(acac)_2$ in 15 ml of methanol. After the catalyst layer 31 is formed, the catalyst-covered substrate 30 is heated to above 900 C in a flow of methane (e.g., as discussed above).

FIG. 3B shows an interconnected film 32 of single-walled carbon nanotubes on the substrate grown from the catalyzed reaction of the methane. Two metal electrodes 33 and 34 are formed over the substrate 30 using, for example, evaporation with a shadow mask (not shown) and with a metal-free gap being between the two electrodes 33 and 34. In one implementation, one or both of the metal electrodes 33 and 34 includes about 20 nanometers of titanium with about 60 nanometers of gold formed thereon. In another implementation, one or both of the metal electrodes are made of an alloy, such as nickel-gold or titanium-gold. In other implementations, the nanotube film 32 is chemically and/or physically modified, such as by coating the nanotube film 32 with materials such as metals or biological molecules. Such modification may, for example, be effected to impart sensitivity of the nanotube film 32 to selected chemical or biological species. In one particular implementation, the nanotube is modified by coupling one or molecules to the nanotube that cause a charge transfer between the nanotube and the molecules, such as via electron withdrawal (e.g., using $NO_2$ or $O_2$) or electron donation (e.g., using $NH_3$). The charge transfer leads to a change in the electrical conductance of the nanotube. With these approaches, nanotube film devices can be easily produced in a scaled-up fashion with low cost.

The nanotube devices described above can be further physically or chemically modified, so as to be tailored for a particular application. For instance, in connection with an example embodiment of the present invention, it has been discovered that a semiconducting or metallic carbon nanotube exhibits a change in electrical conductance when exposed to certain chemical gases. This change may, for example, result from adsorption of the gas particles on the nanotube. It has further been discovered that, by depositing one or more sensing agents onto the nanotube, sensitivity of the nanotube to a wide range of chemical and biological species can be achieved. Furthermore, the sensing agent(s) can be chosen to cause a response of the nanotube to selected molecules (e.g., so that the nanotube exhibits particular characteristics when exposed to the selected molecules). The selectivity of the nanotube to chemical species can be also tuned, or changed, by applying a gating voltage to the nanotube, for example, via the gate 29 adjacent to the nanotube 20 in FIG. 2. The gating voltage effectively shifts the Fermi energy level of the nanotube, enabling the nanotube to be more responsive to a particular species. In one particular implementation, a gating voltage in the range of about −20 to 20 volts is applied to the nanotube. The embodiments described hereinafter demonstrate example functionality and versatility of nanotubes and nanotube devices to which the present invention is directed.

Figure 4A:
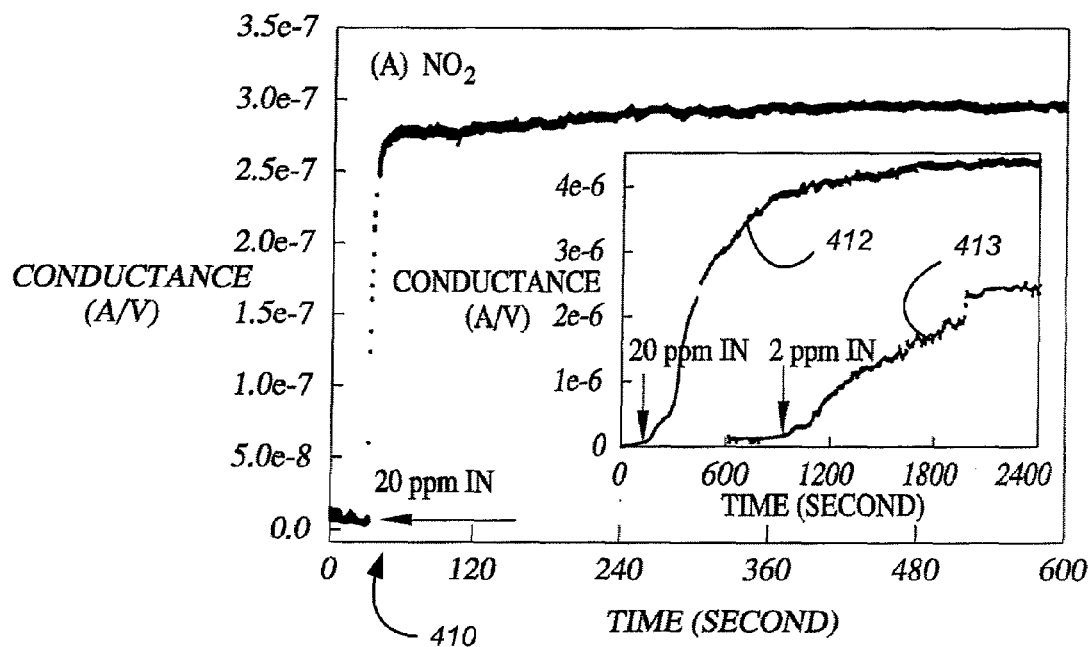
FIGS. 4A-4B show the electrical response of a single nanotube device to $NO_2$ and $NH_3$, respectively, according to other example embodiments of the present invention.
Figure 4B:
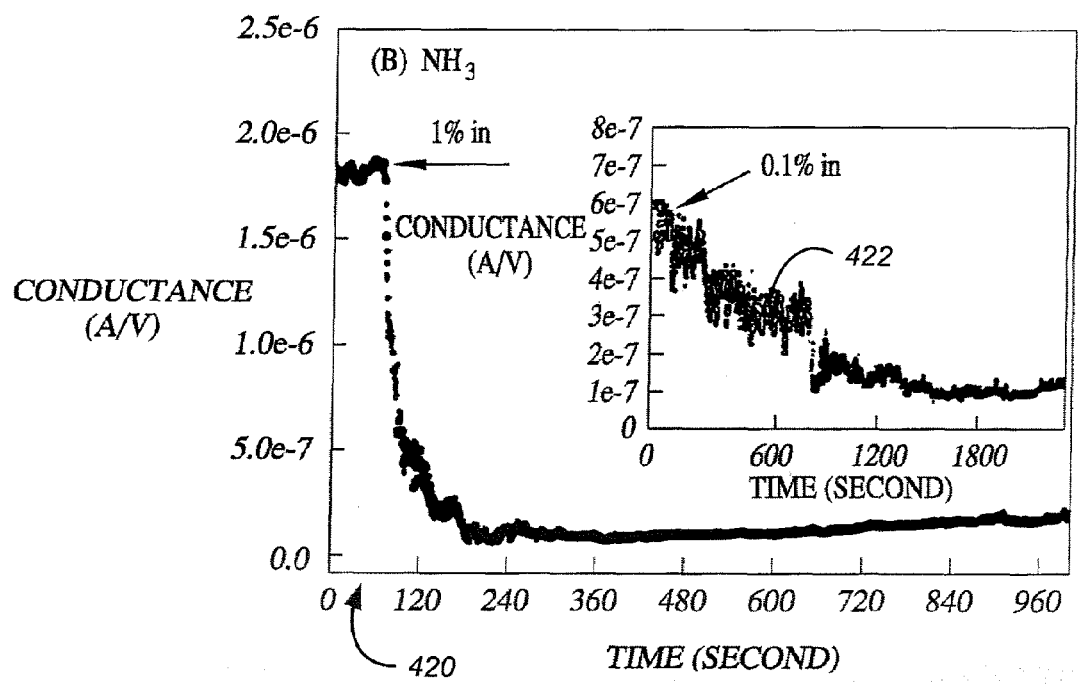

FIGS. 4A and 4B show electrical responses (conductance versus time) of a device including a semiconducting single-walled carbon nanotube to various amounts of $NO_2$ and $NH_3$ gas, respectively, according other example embodiments of the present invention. The electrical responses shown may, for example, be obtained using the nanotube device 200 of FIG. 2, wherein the nanotube 20 is a single-walled carbon nanotube. In one implementation, the single-walled carbon nanotube device is placed in an enclosure, such as a glass flask, equipped with electrical feedthrough (e.g., electrical couplers extending to the carbon nanotube, such as via the electrodes 23 and 26 in FIG. 2). The electrical feedthrough can be used to make electrical connections between the single-walled carbon nanotube device and electrical detection circuits outside the enclosure. A carrier gas (e.g., Ar or air), diluted with $NO_2$ or $NH_3$, is flowed through the flask while the electrical response of the nanotube is detected. The single-walled carbon nanotube device exhibits fast and significant response to the introduction of 20 ppm $NO_2$ and a mixture including 1% $NH_3$, respectively, shown at introduction points 410 in FIG. 4A and 420 in FIG. 4B. In addition, the inset in FIG. 4A shows a comparison of the resulting change in conductance of the single-walled carbon nanotube device when mixtures of 20 ppm and 2 ppm of $NO_2$ at curves 412 and 413, respectively, are introduced. Similarly, curve 422 in FIG. 4B shows the response of the single-walled carbon nanotube device when exposed to a mixture of about 0.1% $NH_3$.

In connection with another example embodiment of the present invention, it has been discovered that the electrical characteristics of a nanotube exposed to a gas, such as shown in FIGS. 4A-4B, is able to fully recover in a flow of pure carrier gas over a period of several hours. In this regard, a pure carrier gas is flowed over a nanotube device after being used to detect the presence of a gas. The pure carrier gas effectively removes interaction of the gas being detected with the nanotube device, and the electrical characteristics of the nanotube device return to that exhibited before introduction of gas. For example, in connection with FIG. 4A, the pure carrier gas is flowed such that the single-walled carbon nanotube device returns to a conductance near 0.0, where it was before the introduction of the $NO_2$. Similarly, in connection with FIG. 4A, the carrier gas is flowed such that the single-walled carbon nanotube device returns to a conductance of about 1.7e-6, where it was before the introduction of the $NH_3$. With these approaches, nanotube devices can be implemented as reusable sensors, with recovery enhanced by the flow of a pure carrier gas.

Figure 5:
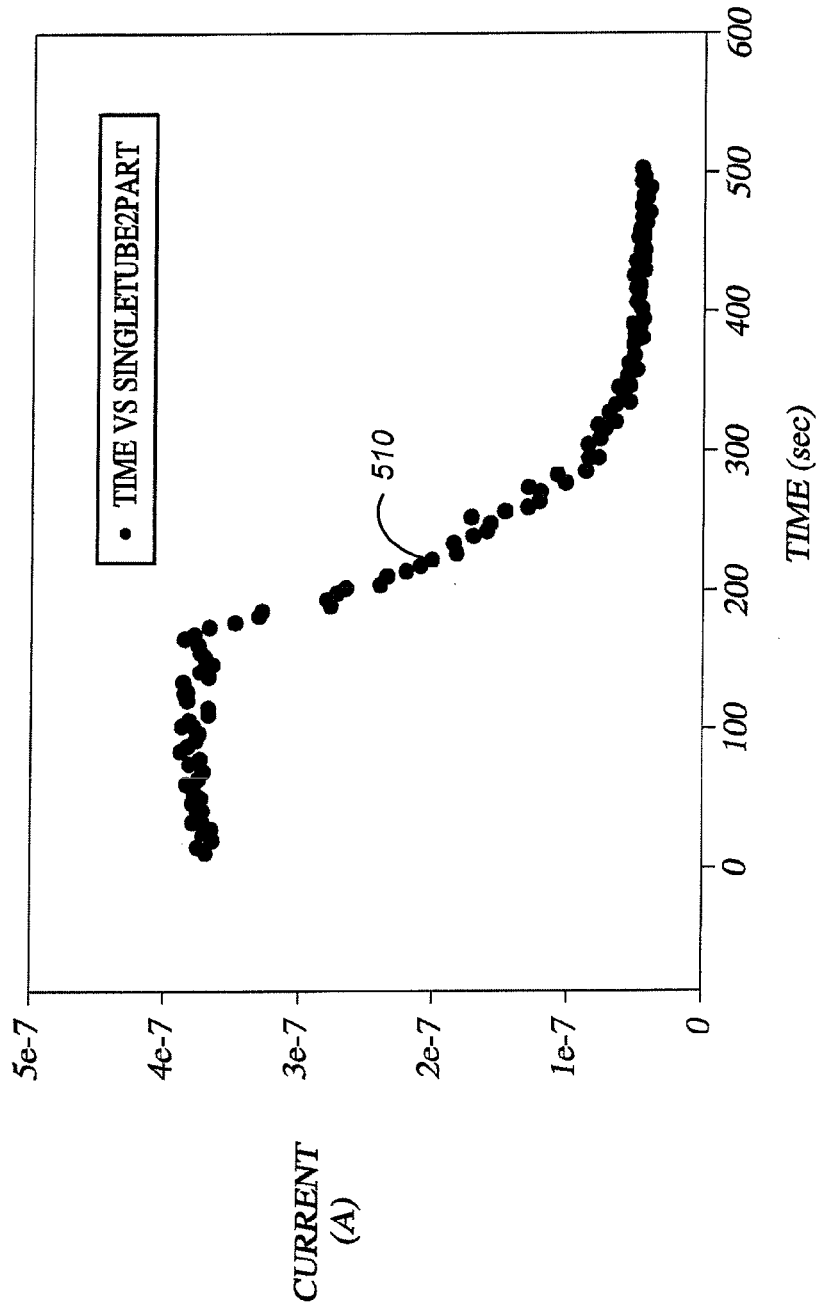
FIG. 5 shows the electrical response of a gold-decorated single nanotube device exposed to thiol vapor, according to another example embodiment of the present invention.

FIG. 5 shows an electrical response curve 510 of current versus time for a gold-decorated single nanotube to thiol vapor, according to another example embodiment of the present invention. The electrical response curve 510 may, for example, be for the nanotube device 200 shown in FIG. 2 with gold applied to the nanotube 20 as a sensing agent. In one implementation, gold is deposited on a carbon nanotube by evaporation, which decorates the nanotube (e.g., rather than forming a continuous layer on the nanotube, due to the tendency of gold to not wet carbon). The observed response 510 of the nanotube to thiol is affected by the presence of the gold particles.

In a more particular implementation, a layer of thiol is formed on the gold-decorated nanotube discussed in connection with FIG. 5 above, and the nanotube is subsequently used to link to biological molecules, which is facilitated by the thiol layer. The electrical response of the nanotube is detected and used to detect the presence of the biological molecules. With this approach, nanotube devices, such as the device 200 in FIG. 2, can be implemented as a versatile biological sensor.

Figure 6:
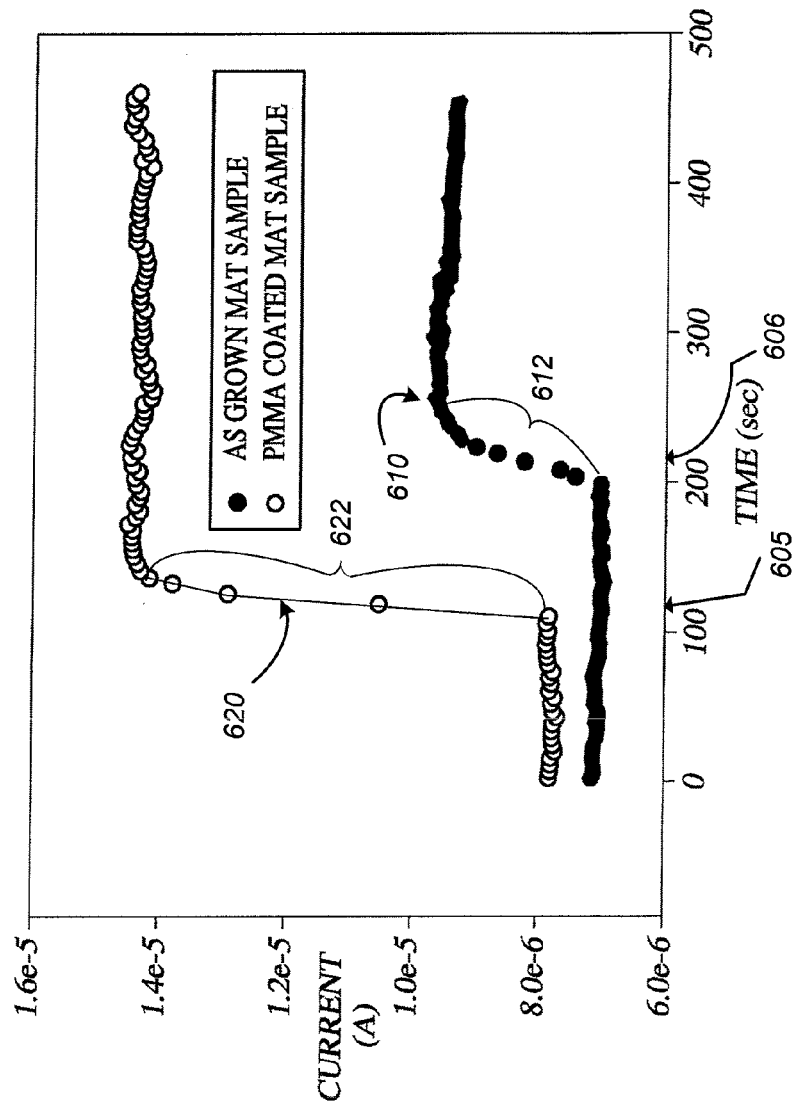
FIG. 6 displays electrical responses of an as-grown nanotube film device and a PMMA-coated nanotube film device exposed to $NO_2$ gas, according to another example embodiment of the present invention.

FIG. 6 shows electrical responses 610 and 620 (current vs. time) of an as-grown nanotube film (e.g., a nanotube mat) device and a PMMA (polymethylmethacrylate)covered nanotube film device to a mixture including about 2 ppm of $NO_2$ gas, respectively, according to another example embodiment of the present invention. The nanotube film device may, for example, include the nanotube film 32 shown in FIG. 3B. In one implementation, the PMMA coating is about 100 nanometers thick, and its presence significantly improves the sensitivity and the response time of the nanotube device to $NO_2$. More specifically, after the introduction of $NO_2$ at point 606, the portion 612 of curve 610 shows a relatively slow response of the device. However, referring to portion 622 of curve 620 for the PMMA-covered nanotube film device, the response at point 605 is relatively faster, with curve portion 620 being nearly vertical. With this approach, the speed at which gasses, such as $NO_2$, can be detected is improved.

Figure 7A:
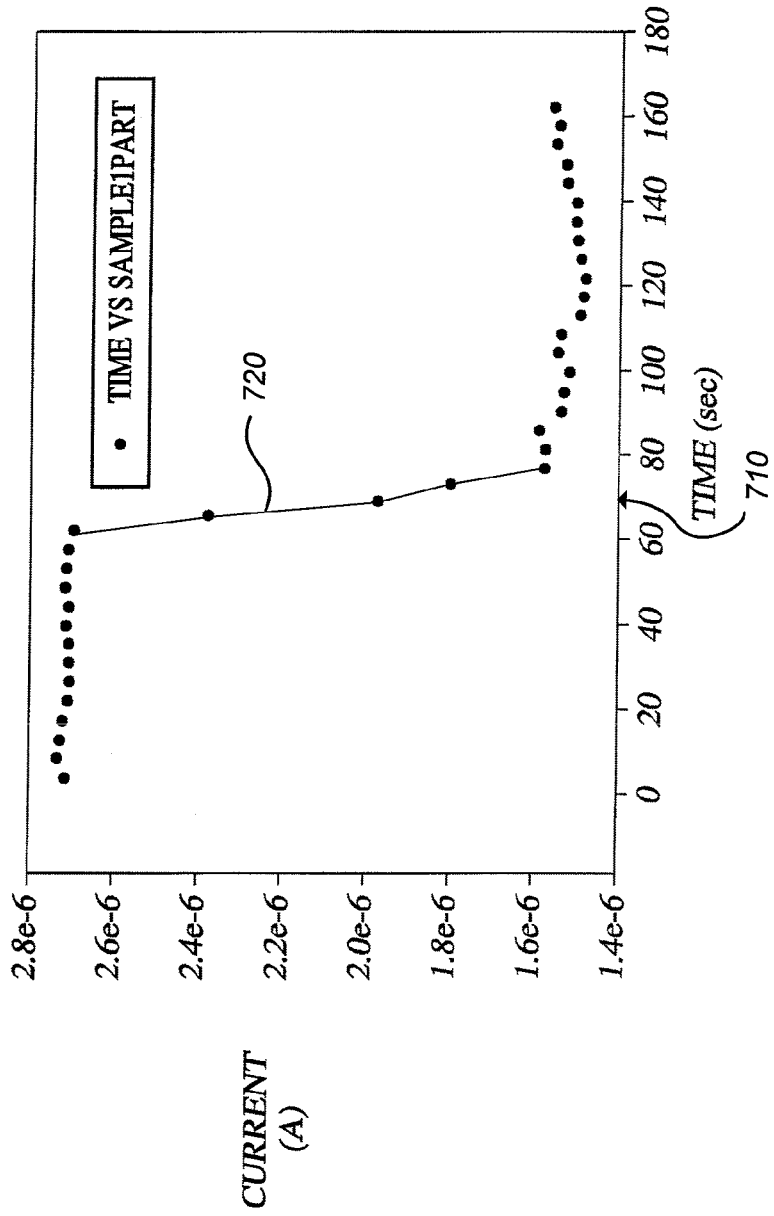
FIGS. 7A-7B show the electrical response of a gold-decorated nanotube film device to thiol vapor and the detection of avidin using a thiol-coated-gold-decorated nanotube film device, according to another example embodiment of the present invention.

FIG. 7A shows the electrical response curve 720 (current vs. time) of a gold-decorated nanotube film device to thiol vapor, according to another example embodiment of the present invention. In this example embodiment, gold particles are first evaporated onto a nanotube film, such as the film 32 in FIG. 3B, and a monolayer of thiol with carboxylic functional group is subsequently attached to the nanotube film. The presence of thiol modifies the electrical conductance of the nanotube device, with the resulting curve 720 shown with the introduction of thiol vapor at point 710.

Figure 7B:
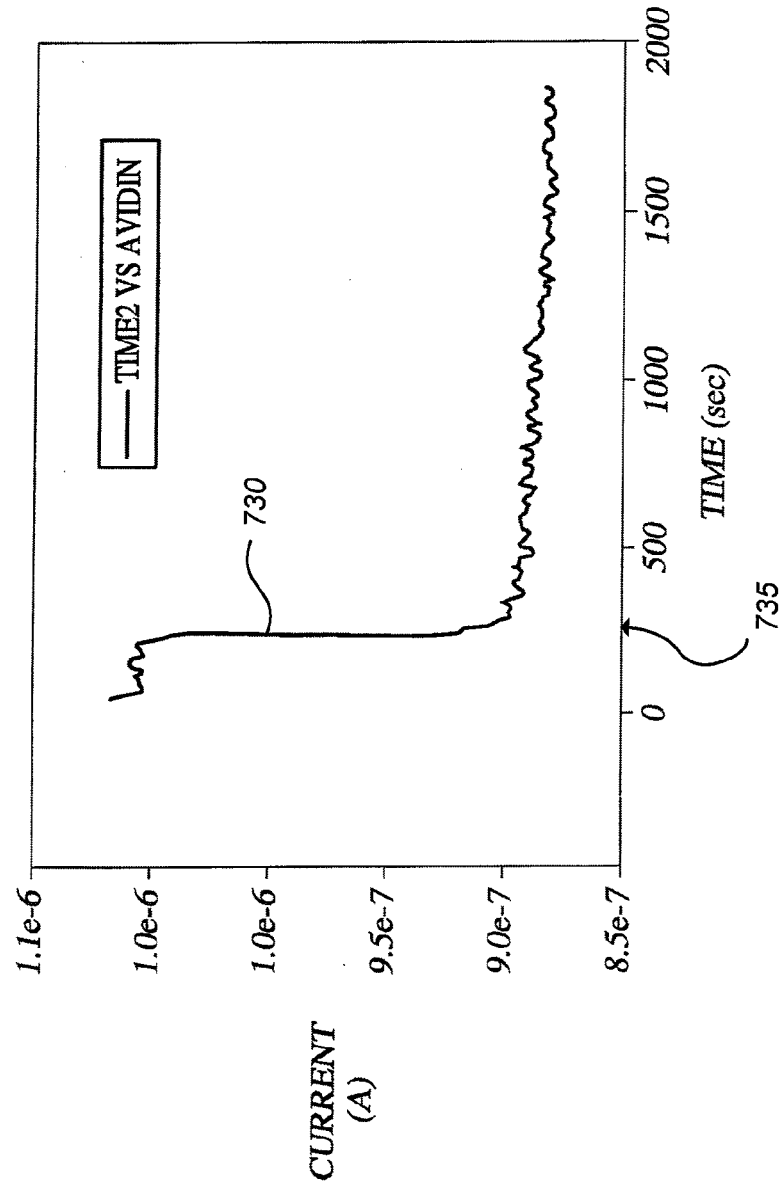

FIG. 7B shows the detection of avidin (a protein) using a thiol-coated-gold-decorated nanotube film device, such as the device discussed in connection with FIG. 7A, according to another example embodiment of the present invention. It has been discovered that, when exposed to avidin, the carboxylic groups of thiol molecules on the thiol-coated-gold-decorated nanotube film device link to avidin molecules via carbodimide chemistry. This link to avidin molecules gives rise to a change in electrical conductance of the nanotube film device, shown by curve 730, with the introduction of the avidin molecules occurring at point 735. In one implementation, the nanotube device is disposed in a liquid environment during introduction of the avidin. In further implementations, additional proteins are detected using a similarly-coated nanotube device in a manner not inconsistent with those described herein.

Figure 8:
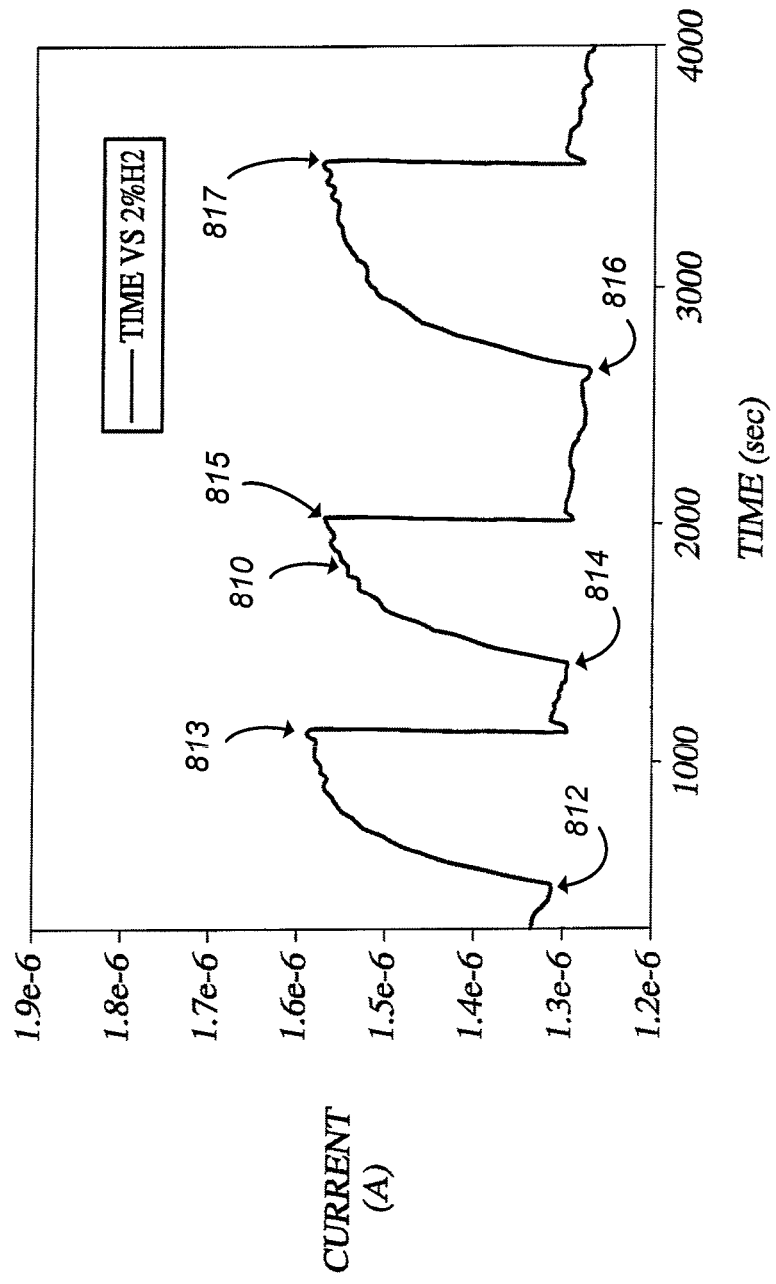
FIG. 8 displays the detection of $H_2$ using a palladium-modified nanotube film device, according to another example embodiment of the present invention.

FIG. 8 shows the detection of $H_2$ using a Palladium-modified nanotube film device, according to another example embodiment of the present invention. Palladium particles are deposited onto and decorate a nanotube film, such as film 32 shown in FIG. 3B, with electrodes 33 and 34 being used for detecting an electrical characteristic of the film 32. It has been discovered that the Palladium-decorated nanotube responds to $H_2$ molecules. This response can be used to detect the presence of the $H_2$ molecules. In this regard, curve 810 shows the response (current vs. time) of the nanotube film with the introduction of a mixture having about 2% $H_2$ molecules in dry air at curve portions 812, 814 and 816. The nanotube device recovers when the $H_2$ is removed (e.g., with dry air or other pure carrier gas being flowed across the device), as shown at curve portions 813, 815 and 817.

In another example embodiment of the present invention, an enzyme is attached to a nanotube or a nanotube film, such as the nanotube 20 in FIG. 2 and/or the nanotube film 32 in FIG. 3B. It has been discovered that such an enzyme-coated nanotube or nanotube film exhibits changes in its electrical conductance when exposed to glucose and to biological species. With this approach, nanotube and nanotube film-based sensors, such as those described above, employing enzyme-coated nanotubes can be used for detecting glucose and/or biological species, which is particularly useful in a variety of medical applications.

In other example embodiments of the present invention, various other materials are used to modify the electrical response of nanotubes and/or nanotube films in a manner similar to one or more of the example embodiments and implementations described herein. For instance, a carbon nanotube can be modified to respond electrically to CO. Such an electrical response is useful, for example, for detecting the presence and/or quantity of CO in the exhaust of internal combustion engines.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include modifying the nanotubes for sensing one or more particular molecular species, altering the circuit arrangements, interchanging nanotube films and single nanotubes, and where appropriate, using SWNTs as building blocks for more complex devices. Moreover, in addition to the sensing agents described in the example embodiments and implementations above, other materials can be applied to the nanotubes and nanotube devices for tailoring their application. For example, metal particles (e.g., nickel, rhodium, palladium, $TiO_2$), polymers, and biological species are used as sensing agents in various implementations to modify the sensitivity of nanotubes to chemical and biological species. Furthermore, the nanotubes may be made of materials other than carbon, such as silicon and/or boron, which can also be grown using a synthesis process similar to that described above. Such modifications and changes do not depart from the true spirit and scope of the present invention, which is set forth in the following claims.

What is claimed is:

1. A nanotube device comprising: first and second conducting elements and at least one nanotube adapted to pass current between the first and second conducting elements, wherein a first end of said at least one nanotube is in electrical contact with the first conducting element and a second end of said at least one nanotube is in electrical contact with the second conducting element, and wherein at least one end of the at least one nanotube is rooted in a catalyst island.

2. The nanotube device of claim 1, wherein said nanotube is a carbon nanotube.

3. The nanotube device of claim 2, wherein said nanotube is a single-walled nanotube.

4. The nanotube device of claim 1, wherein said nanotube includes silicon.

5. The nanotube device of claim 1, wherein said nanotube is semiconducting between said first and second conducting elements.

6. The nanotube device of claim 1, wherein said nanotube includes metal.

7. The nanotube device of claim 1, wherein said nanotube is disposed on a surface.

8. The nanotube device of claim 7, wherein said surface is a top surface of a substrate comprising a material selected from a group consisting of silicon, alumina, quartz, silica and silicon nitride.

9. The nanotube device of claim 8, wherein said substrate comprises doped silicon covered with a layer of native oxide.

10. The nanotube device of claim 7, further comprising a gate in the surface and configured and arranged to apply a gating voltage to the nanotube 11. The nanotube device of claim 1, wherein at least one of said first and second conducting elements comprises a catalyst island covered by a metal electrode, and wherein at least one of said ends of said nanotube is rooted in said catalyst island and covered by said metal electrode.

12. The nanotube device of claim 11, wherein said catalyst island comprises a material selected from a group consisting of iron, molybdenum, cobalt, nickel, ruthenium, zinc and oxides thereof.

13. The nanotube device of claim 11, wherein said catalyst island comprises $Fe_2O_3$ and alumina nanoparticles.

14. The nanotube device of claim 11, wherein said catalyst island is between about 3-5 microns wide.

15. The nanotube device of claim 11, wherein said metal electrode comprises an alloy of nickel-gold.

16. The nanotube device of claim 11, wherein said metal electrode comprises an alloy of titanium-gold.

17. The nanotube device of claim 1, wherein at least one of said conducting elements comprises a metal pad covering at least one of said ends of said nanotube.

18. The nanotube device of claim 17, wherein said metal pad comprises a material selected from the group consisting of titanium, gold, aluminum, chromium, and platinum.

19. The nanotube device of claim 1, further comprising one or more sensing agents attached to said nanotube.

20. The nanotube device of claim 19, wherein, upon exposure to a selected molecule, the nanotube exhibits an electrical response that is a function of the one or more sensing agents.

21. The nanotube device of claim 19, wherein the one or more sensing agents includes metal.

22. The nanotube device of claim 19, wherein the electrical conductance of the nanotube is a function of the one or more sensing agents.

23. The nanotube device of claim 1, wherein the at least one nanotube extends from a catalyst material.

24. The nanotube device of claim 23, wherein the catalyst material is disposed on a substrate.

25. The nanotube device of claim 23, wherein the catalyst material is the first conducting element.

26. The nanotube device of claim 23, wherein the catalyst material is the second conducting element.

27. The nanotube device of claim 1, further comprising a gate disposed adjacent to the nanotube and adapted to apply a gating voltage to the nanotube.

28. The nanotube device of claim 27, wherein the gate is further adapted to apply a gating voltage that alters an electrical characteristic of the nanotube.

* * * * *